United States Patent [19]

Schubert et al.

[11] Patent Number: 5,409,935
[45] Date of Patent: Apr. 25, 1995

[54] XANTHINE DERIVATIVES FOR THE TREATMENT OF SECONDARY NERVE CELL DAMAGE AND FUNCTIONAL DISORDERS AFTER CRANIO-CEREBRAL TRAUMAS

[75] Inventors: Hans-Peter Schubert, Apfeldorf; John J. Grome; Barbara Kittner, both of Wiesbaden; Karl Rudolphi, Mainz; Ulrich Gebert, Schlossborn, all of Germany

[73] Assignee: Hoechst Aktiengesellschaft, Frankfurt am Main, Germany

[21] Appl. No.: 909,389

[22] Filed: Jul. 9, 1992

[30] Foreign Application Priority Data

Jul. 11, 1991 [DE] Germany ............ 41 22 884.7
May 28, 1992 [DE] Germany ............ 42 17 639.5

[51] Int. Cl.$^6$ ............ A61K 31/52; C07D 473/04
[52] U.S. Cl. ............ 514/265; 544/267; 544/270; 544/271
[58] Field of Search ............ 544/270, 271, 267; 514/265

[56] References Cited

U.S. PATENT DOCUMENTS

| | | | |
|---|---|---|---|
| 4,275,064 | 6/1981 | Bodor et al. | 544/267 |
| 4,289,776 | 9/1981 | Mohler et al. | 544/271 |
| 4,291,037 | 9/1981 | Brenner et al. | 544/271 |
| 4,719,212 | 1/1988 | Goto et al. | 514/263 |
| 4,833,146 | 5/1989 | Gebert et al. | 544/267 |
| 4,868,186 | 9/1989 | Franzone et al. | 514/265 |

FOREIGN PATENT DOCUMENTS

WO85/02542 6/1985 WIPO.
WO86/00401 1/1986 WIPO.

OTHER PUBLICATIONS

Chao et al., Activated Microglia Mediate Neuronal Cell Injury Via a Nitric Oxide Mechanism, J. Immunol., 1992 (Abstract).
Woodroofe et al., Detection of Interleukin-1 and Interleukin-6 in Adult Rat Brain, Following Mechanical Injury, by in Vivo Microdialysis: Evidence of Microglia in Cytokine Production, J. Neuroimmunol, 1991 (Abstract).
Giulian D., Microglia, Cytokines, and Cytotoxins: Modulators of Cellular Responses After Injury to the Central Nervous System, EOS Riv. Immunol. Immunofarm, 1990 (Abstract).
Giulian et al., Microglial Mitogens Are Produced in the Developing and Injured Mammalian Brain, J. Cell Biol., 1991 (Abstract).
Giulian et al., Brain Glia Release Factors With Opposing Actions Upon Neuronal Survival, J. Neurosci, 1993 (Abstract).
Giulian, Ameboid Microglia as Effectors of Inflammation in the Central Nervous System, J. Neurosci. Res., 1987 (Abstract).

(List continued on next page.)

Primary Examiner—Mukund J. Shah
Assistant Examiner—P. K. Sripada
Attorney, Agent, or Firm—Finnegan, Henderson, Farabow, Garrett & Dunner

[57] ABSTRACT

The use of xanthine derivatives for the treatment of secondary nerve cell damage and functional disorders after cranio-cerebral traumas (CCT)

The use of xanthine derivatives of the formula I

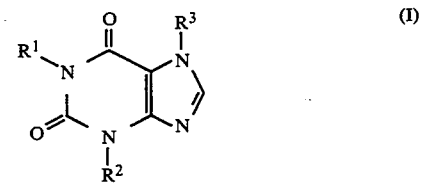

and of their physiologically tolerable salts, in which $R^1$ is oxoalkyl, hydroxyalkyl or alkyl, $R^2$ is hydrogen or alkyl and $R^3$ is hydrogen, alkyl, oxoalkyl or an alkyl having up to 6 carbon atoms, whose carbon chain is interrupted by an oxygen atom, for the production of pharmaceuticals for the treatment of disorders which can occur after cranio-cerebral traumas is described.

14 Claims, No Drawings

OTHER PUBLICATIONS

Frei et al., Immunobiology of Microglial Cells, Ann. New York Acad. Sci., 1988 (Abstract).

Adams et al., Head Injury, Greenfield's Neuropathology, Fourth Edition, pp. 85–124, 1984.

Lister, "Fused Pyrimidines" Part II, Purines, The Oxo-(Hydroxy-) and Alkoxypurines, pp. 223–225, 1971.

Lister, "Fused Pyrimidines" Part II, Purines, Chapter II, Syntheses From Pyrimidines, pp. 31, 35 and 55, 1971.

Krauch et al., Reaktionen Der Organischen Chemie, Traurr, p. 590, 1971.

Glia, "Functional Plasticity of Microglia: A Review", vol. 1, pp. 301–307, 1988.

E. Pfenninger, Das Schadel–Hirn–Trauma, Anaesthesiologie und Intensivmedizin, vol. 203, Bergmann (Editor), Springer-Verlay, Berlin, 1988.

Banati et al., "Respiratory burst activity in brain macrophages: a flow cytometric study on cultured rat microglia", Neuropathology and Applied Neurobiology, vol. 17, pp. 223–230, 1991.

Head Injury: Hope Through Research, NIH Publication No. 84–2478, Aug. 1984.

DeLeo et al., "Protection Against Ischemic Brain Damage Using Propentofylline in Gerbils," Stroke, vol. 19, No. 12, pp. 1535–1539, 1988.

Stefanovich et al., "Effect of Propentofylline on the Biochemical Lesion of the Rat Brain in Aluminium-Induced Neurotoxidity," Metobolic Brain Disease, vol. 5, No. 1, pp. 7–17, 1990.

Mrsulja et al., "Propentofylline and Postischemic Brain Edema: Relation to $Na+-K+-$ATPase Activity," Drug Development Research, vol. 6, No. 4, pp. 339–344, 1985.

Ganser et al., "Effect of Pentoxifylline on Cerebral Edema in Cats," Neurology, vol. 24, No. 5, pp. 487–493, 1974.

Shinoda et al., "Stimulation of Nerve Growth Factor Synthesis/Secretion By Propentofylline in Cultured Mouse Astroglial Cells," Biochemical Pharmacology, vol. 39, No. 11, pp. 1813–1816, 1990.

Mann et al., "The Synthesis and Properties of 1:7-Dialkyl Xanthines," J. Chem. Soc., pp. 751–760, 1945.

Robert Berkow "The Merck Manual", published by Merck, Sharp & Dohme Research Laboratories, pp. 1334–1337, 1982.

XANTHINE DERIVATIVES FOR THE TREATMENT OF SECONDARY NERVE CELL DAMAGE AND FUNCTIONAL DISORDERS AFTER CRANIO-CEREBRAL TRAUMAS

A number of oxoalkyl- and hydroxyalkylxanthines have a blood flow-stimulating action and can also be employed in cerebral circulatory disorders (U.S. Pat. No. 4,289,776, PCT 86/00401, U.S. Pat. No. 3,737,433). Thus, it is known that 1-(5-oxohexyl)-3-methyl-7-n-propylxanthine (compound 1), owing to its vasodilating action combined with low toxicity, is suitable for the treatment of patients who suffer from arterial circulatory disorders. Processes for the preparation of these compounds are also described therein (U.S. Pat. No. 4,289,776).

In U.S. Pat. No. 4,719,212, the use of 1-(5-oxohexyl)-3-methyl-7-n-propylxanthine for the treatment of memory disorders is described.

Cranio-cerebral traumas (CCT) are statistically important as a cause of accidental death or permanent brain damage. About 30% of all injured people in road traffic accidents suffer CCT which require in-patient treatment. Annually in the Federal Republic of Germany about 150,000 CCT have to be expected in any type of accident and the number of deaths is about 14,000. In the USA the death rate due to CCT is about 34,000/year. Many of the surviving CCT victims suffer long-lasting health disorders or permanent disabilities leading up to inability to earn a living and permanent care. The effects on social medicine and the national economy are immense, in particular as the majority of the affected are road traffic accident victims of relatively young age.

Diagnostically, there is a differentiation between open and closed (covered) CCTs. Open is understood as meaning all injuries in which the cerebral meninges (Dura mater) is opened and the brain is in contact with the outside world through this opening. This application does not relate to this type of CCT but rather to closed CCT. In this, local lesions (for example contusions or hematomas) and diffuse cerebral tissue damage occur. The latter extend from the primarily traumatized area to other cerebral areas and, depending on localization and severity, can lead to reversible or permanent disorders of cerebral function of a sensory, motor or intellectual type. Often, after CCT a loss of consciousness occurs which can change to a comatose condition. The primary damage after tissue destruction in the brain is irreparable, but only responsible in rare cases for the fatal outcome. Principal causes of permanent disability or death are rather the formation and the extent of the secondary brain damage, which are potentially reversible and can be influenced therapeutically. In 90% of all patients who die of CCT secondary lesions are detectable.

To date, there are no pharmaceuticals known which offer effective protection against the formation of secondary brain damage. Clinical trials with barbiturates and calcium antagonists were unsuccessful. The treatment of patients with severe CCT is therefore restricted at present to conventional intensive care measures such as stabilization of the cardiovascular system and respiration and if appropriate the control of the intracerebral pressure by means of diuretics or osmotherapeutics. Later, physiotherapeutic and logopedic rehabilitation measures begin.

The severity and the extent of the post-traumatic secondary brain damage depend on the extent of the primary trauma and on the type and timing of medical care. The pathogenesis of post-traumatic secondary damage is complex and leads, inter alia, finally to a greatly increased intracranial pressure (diffuse cerebral edema) and to necrosis of the extremely vulnerable nerve cells (Pfenninger, E. 1988, Cranio-cerebral Trauma. In: H. Bergmann (Editor) Anaesthesiologie und Intensivmedizin (Anesthesiology and Intensive Medicine) Vol. 203, Springer-Verlag, Berlin and Head Injury: Hope through research, 1984, U.S. Dept. of Health and Human Services, National Institutes of Health Publication No. 84-2478).

The essential pathogenetic factor for tissue death discussed in the more recent literature is the formation of macrophages which release a number of histotoxic substances, in particular oxygen free radicals. Macrophages are formed in the course of activation of the immune system. They are formed not only from stimulated blood cells forming free radicals, but in the brain also from activated microglia cells, which besides proteolytic enzymes produce free radicals to a particularly great extent (Banati et al.; Glia, 1991). As increased free radical formation can apparently lead to damage of cell functions and the neurotoxic action of macrophages is discussed causally in connection with nerve cell death, compounds which inhibit the free radical formation in cerebral macrophages can be employed therapeutically in the neurological clinic. The activation of microglia cells and/or the occurrence of macrophages is observed in a multiplicity of neuropathological processes which accompany the death of cerebral tissue (Streit et al. Glia 1, (1988), 301), inter alia in the course of post-traumatic secondary brain damage.

Surprisingly, xanthine derivatives of the formula I exhibit a potent inhibition of free radical formation, to be precise both in peripheral (peritoneal) macrophages and in cultures of activated microglia cells of the brain.

The invention therefore relates to the use of xanthine derivatives of the formula I

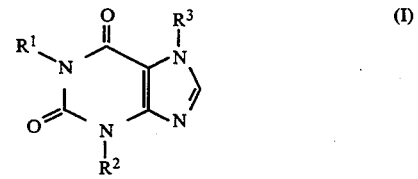

and/or their physiologically tolerable salts, in which $R^1$ is a) oxoalkyl having 3 to 8 carbon atoms, whose carbon chain can be straight-chain or branched,
b) hydroxyalkyl having 1 to 8 carbon atoms, whose carbon chain can be straight-chain or branched and whose hydroxyl group is a primary, secondary or tertiary alcohol function, or
c) alkyl having 1 to 6 carbon atoms, whose carbon chain can be straight-chain or branched, $R^2$ is a) hydrogen or
b) alkyl having 1 to 4 carbon atoms, whose carbon chain can be straight-chain or branched, $R^3$ is a) hydrogen, b) alkyl having 1 to 6 carbon atoms, whose carbon chain can be straight-chain or branched,
c) alkyl having 1 to 6 carbon atoms, whose carbon chain is interrupted by an oxygen atom, or
d) oxoalkyl having 3 to 8 carbon atoms, whose carbon chain can be straight-chain or branched, for the production of pharmaceuticals for the treatment of disorders which can occur after cranio-cerebral traumas.

Preferably, xanthine derivatives of the formula I are used in which
$R^1$ is
a) oxoalkyl having 4 to 6 carbon atoms, whose carbon chain is straight-chain, or
b) alkyl having 3 to 6 carbon atoms,
$R^2$ is alkyl having 1 to 4 carbon atoms,
$R^3$ is
a) alkyl having 1 to 4 carbon atoms or
b) oxoalkyl having 3 to 6 carbon atoms.

Particularly preferably, 1-(5-oxohexyl)-3-methyl-7-n-propylxanthine is used. Examples which may be mentioned are the following compounds of the formula I:
1-(5-hydroxy-5-methyl-hexyl)-3-methylxanthine,
7-(ethoxymethyl-1-(5-hydroxy-5-methyl-hexyl)-3-methylxanthine,
1-(5-oxohexyl)-3,7-dimethylxanthine,
7-(2-oxopropyl)-1,3-di-n-butylxanthine or
1-hexyl-3,7-dimethylxanthine.

Suitable physiologically tolerable salts of the xanthine derivatives of the formula I are, for example, alkali metal, alkaline earth metal or ammonium salts, including those of physiologically tolerable organic ammonium bases.

The invention also relates to novel xanthine derivatives of the formula I

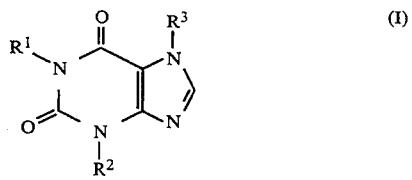

in which
$R^1$ is
a) oxoalkyl having 3 to 8 carbon atoms, whose carbon chain can be straight-chain or branched,
b) hydroxyalkyl having 1 to 8 carbon atoms, whose carbon chain can be straight-chain or branched and whose hydroxyl group is a primary, secondary or tertiary alcohol function, or
c) alkyl having 1 to 6 carbon atoms, whose carbon chain can be straight-chain or branched,
$R^2$ is hydrogen,
$R^3$ is
a) hydrogen,
b) alkyl having 1 to 6 carbon atoms, whose carbon chain can be straight-chain or branched,
c) alkyl having 1 to 6 carbon atoms, whose carbon chain is interrupted by an oxygen atom, or
d) oxoalkyl having 3 to 8 carbon atoms, whose carbon chain can be straight-chain or branched.

Preferred xanthine derivatives of the formula I are those in which
$R^1$ is hydroxyalkyl having 1 to 8 carbon atoms, whose carbon chain can be straight-chain or branched and whose hydroxyl group is a primary, secondary or tertiary alcohol function,
$R^2$ is hydrogen,
$R^3$ is
a) hydrogen,
b) alkyl having 1 to 6 carbon atoms, whose carbon chain is interrupted by an oxygen atom.

The xanthine derivatives of the formula I can be prepared by the following processes:
a) Reaction of alkali metal salts of 3-monoalkyl- or 1,3- or 3,7-dialkylxanthines with a compound of the formula II

in which A is an alkyl group having 1 to 6 carbon atoms and X is halogen, such as fluorine, chlorine, bromine or iodine, under basic conditions,
b) Reaction of a 3-monoalkyl- or 3,7-dialkylxanthine with a compound of the formula III

in which X and A have the meaning given in a) and $R^4$ is hydrogen and/or methyl, under basic conditions
c) Reaction of alkali metal salts of 3-monoalkyl- or 1,3- or 3,7-dialkylxanthines with an appropriate alkyl halide in a solvent under basic conditions
d) Reaction of alkali metal salts of 3-monoalkyl- or 1,3-dialkylxanthines with a compound of the formula IV

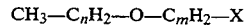

in which n is an integer from 0 to 4 and m is an integer from 1 to 5, with the stipulation that n and m together are not more than 5, and X is defined as in a), under basic conditions,
e) Reaction of xanthines protected on $R^2$ and $R^3$ with a compound of the formula II or formula III or an alkyl halide having up to 6 carbon atoms, under basic conditions, where A, X and $R^4$ have the meaning mentioned in b), and subsequent removal of the protective group(s),
f) Reaction of alkali metal salts of 3-monoalkylxanthines or of xanthines protected on $R^2$ with a compound of the formula II or formula IV or an alkyl halide having up to 6 carbon atoms to give a correspondingly 3,7-substituted xanthine, subsequent reaction with a compound of the formula II or formula III or an alkyl halide having up to 6 carbon atoms and subsequent removal of the protective group which may be present.

The abovementioned reactions are carried out under standard conditions in a known manner (U.S. Pat. No. 4,289,776, PCT/EP86/00401, U.S. Pat. No. 3,737,433).

Xanthines protected on $R^2$ or on $R^2$ and $R^3$ are understood as meaning xanthines which carry protective groups such as benzyl, diphenylmethyl or 4-methoxybenzyl in the position of $R^2$ or $R^2$ and $R^3$. The protective groups are removed as described, for example, in U.S. Pat. No. 4,833,146.

The starting substances for the reactions are known or can easily be prepared by methods known from the literature.

The invention also relates to pharmaceuticals which comprise at least one xanthine derivative of the formula I and/or at least one of its physiologically tolerable salts, and in addition to pharmaceutically suitable and physiologically tolerable excipients, diluents also contain other active substances and auxiliaries.

The invention also relates to a process for the preparation of a pharmaceutical according to the invention, which comprises bringing at least one xanthine derivative of the formula I into a suitable administration form using a pharmaceutically suitable and physiologically tolerable excipient and, if appropriate, other suitable active substances, additives or auxiliaries.

The pharmaceuticals according to the invention can be administered orally, topically, rectally, intravenously or if desired also parenterally. Administration is carried out after a CCT.

Suitable solid or liquid pharmaceutical administration forms are, for example, granules, powders, coated tablets, tablets, (micro)capsules, suppositories, syrups, juices, suspensions, emulsions, drops or injectable solutions and also preparations with protracted release of active substance, in whose preparation customary auxiliaries, such as excipients, disintegrants, binders, coating agents, swelling agents, lubricants, flavorings, sweeteners or solubilizers are used. Commonly used auxiliaries which may be mentioned are, for example, magnesium carbonate, titanium dioxide, lactose, mannitol and other sugars, talc, milk protein, gelatin, starch, cellulose and its derivatives, animal and vegetable oils, polyethylene glycols and solvents, such as, for example, sterile water and mono- or polyhydric alcohols, for example glycerol.

Preferably, the pharmaceutical preparations are prepared and administered in dosage units, each unit containing as active constituent a specified dose of at least one of the xanthine derivatives of the formula I and/or at least one of their physiologically tolerable salts. In the case of solid dosage units, such as tablets, capsules, coated tablets or suppositories, this dose can be up to about 300 mg, but preferably about 10 to 100 mg. For the treatment of a patient (70 kg) who has suffered a CCT, in the early phases after the CCT an intravenous infusion treatment of at most 1200 mg per day and in the later rehabilitation phase an oral administration of 3 times 300 mg per day of the compound 1 and/or of the corresponding salts of the compound 1 is indicated.

Under certain circumstances, however, higher doses or lower doses may also be appropriate. The administration of the dose can be carried out either in the form of an individual dosage unit or else of several smaller dosage units, or by repeated administration of subdivided doses at specific intervals.

Finally, the xanthine derivatives of the formula I and/or their corresponding salts can also be formulated in the production of the abovementioned pharmaceutical administration forms together with other suitable active substances, for example active substances which entrain oxygen free radicals, for example 4H-pyrazolo-[3,4-d]-pyrimidin-4-one-1,5-dihydro or the enzyme superoxide dismutase.

EXAMPLE 1

Pharmacological tests and results

In order to measure the intracellular generation of oxygen free radicals in peritoneal macrophages and in cultures of activated microglia, a flow-cytometric method was used (Rothe, Oser, Valet, Naturwissenschaften, 75, 354, 1988). Specifically, the free radical formation in individual viable cells was determined by measuring the intracellular oxidation of the membrane-permeable and non-fluorescent Dihydrorhodamine 123 (DHR; Eugene, Ore., USA) to the membrane-impermeable and intracellularly "trapped", green fluorescent Rhodamine 123.

DHR was dissolved in a 43.3 mM stock solution in N,N-dimethylformamide (DMF; Merck, Darmstadt, F.R.G.). The method is also suitable for the individual and simultaneous measurement of various subpopulations within a heterogeneous cell population; it therefore allows the exclusion of contaminating populations. Moreover, in another series of tests the identification of the cell type to be measured in each case was simultaneously confirmed during the flow-cytometric measurement by specific immunocytochemical antibody staining. Peritoneal macrophages were obtained by peritoneal washing of white male Wistar rats aged 12 weeks with 10 ml of HBS-Hanks (Serva Feinbiochemica, Heidelberg). The cells were sedimented at 200 g and 20° C. for 5 min and resuspended in HBS-Hanks ($4 \times 10^6$ cells/ml). All cells were stored for a period of at most 2 hours after preparation until flow-cytometric analysis at 4° C.

Before the start of measurement, all cells (the macrophage suspension (10 $\mu$l) was additionally diluted with 1 ml of HBS-Hanks) were stained with 1 $\mu$l of the 43.3 mM DHR solution in DMF at 37° C. for 5 min. In order to test the effect of the compound 1, in the experimental groups the DHR-loaded cells were incubated with 10 $\mu$M or 50 $\mu$M of the compound according to the invention for 15, 25, 35, 45 and 60 min, to be precise with or without parallel stimulation of free radical formation by concanavalin A (Sigma Chemie, Deisenhofen, conA, 100 $\mu$M/ml). No active substance was added to the respective control groups.

Microglia cultures from the brain of newborn rats were prepared (Giulian & Baker, J. Neuroscience, 1986, 6:2163–2178). After mechanical dissociation of the tissue in Dulbecco's modified Eagle's medium (Sigma Chemie, DMEM), supplemented with 2 g/l of NaHCO$_3$ and 20% heat-inactivated fetal calf serum, the primary cultures were kept in 75 cm$^3$ culture flasks at 3% pCO$_2$ and 37° C. for 2 to 4 weeks. Cells which grew on the surface of a continuous cell layer were removed by shaking, pelleted and resuspended ($3 \times 10^6$ cells/ml) in Hepes Hanks buffered salt solution (5 mM Hepes, 0.15M NaCl, pH 7.35; Serva Feinbiochemica, Heidelberg, F.R.G.). In order to test the effect of the compound 1, in the experimental groups the DHR-loaded cells were incubated with 50 $\mu$M of the compound according to the invention for 15, 25, 35, 45 and 60 min, to be precise with or without parallel stimulation of free radical formation by concanavalin A (conA, 100 $\mu$M/ml). No active substance was added to the respective control groups.

The cell volume and two fluorescences were simultaneously measured in about 10,000 cells per sample using a FACScan flow cytometer (Becton Dickinson, San Jose, Calif., USA). Rhodamine 123 green fluorescence (500-530 nm) and propidium iodide red fluorescence (590-700 nm) were measured with excitation by an argon laser with a wavelength of 488 nm. The flow cytometer was calibrated with standardized yellow-green-fluorescing microspheres of 4.3 μm diameter (Polysciences, St. Goar, F.R.G.).

Each measurement is based on the individual measurements of the cells contained in a sample (about 10,000). In order to keep the experimental boundary conditions as constant as possible, several experiments were carried out successively on the same day. In such a test series, in each case four different samples of an experimental group and their control were measured by flow cytometry at variously defined points of time. As a rule, 3-4 test series were carried out per experimental group.

A) Action on peritoneal macrophages

Stimulation of peritoneal macrophages with concanavalin A (conA, 100 μg/ml) led to a significant increase in the production of oxygen free radicals, measured as % increase in the green fluorescence after oxidation of Dihydrorhodamine 123 (DHR) to Rhodamine 123. When peritoneal macrophages were measured in the presence of 50 μM compound 1, the stimulatory effect of conA was blocked (Tab. 1). The effect of compound 1 is significant ($p < 0.05$ in the t-test) in all measurements with incubation times over 15 min. The measured % fluorescence of the conA-stimulated peritoneal macrophages was even lower in the presence of 50 μM compound 1 than in the control measurements of non-stimulated macrophages. The suppressive effect of compound 1 on free radical formation was dose-dependent and a significant effect could also be achieved with a compound 1 concentration of 10 μM compound 1. In this case, the % inhibition of 10 μM compound 1 on conA-stimulated macrophages was measured at maximum conA activation. It amounted to 21% at a time of 35 min and was significant ($p < 0.05$ in the t-test).

TABLE 1

Effect of 50 μM compound 1 on free radical formation by conA-stimulated macrophages

| Min | Control | conA | conA ± Comp. 1 | % Inhibition |
|---|---|---|---|---|
| 15 | 4.5025 | 7.7775 | 9.0875 | — |
|  | (0.897) | (1.487) | (0.742) |  |
| 25 | 9.025 | 20.2 | 8.0867 | 60* |
|  | (2.658) | (7.883) | (6.159) |  |
| 35 | 28.988 | 40.47 | 25.5 | 37* |
|  | (2.64) | (0.837) | (1.87) |  |
| 45 | 40.015 | 46.253 | 31.755 | 32* |
|  | (4.54) | (3.12) | (1.59) |  |

The numerical values (mean values ± S.D. in brackets) give the fluorescence values as apparatus-specific units.
*Statistically significantly different from control $p < 0.05$, t-test.

B) Action on microglia cells

In cultivated microglia cells, free radical formation (measured as Rhodamine fluorescence, was considerably higher (about 50-100 fold) than in peritoneal macrophages. As previously described (Banati et al. Glia, 1991), this massive free radical formation in microglia cells cannot be further increased by stimulation with conA. Incubation of the microglia cells with 50 μM compound 1 led to a clear inhibition of free radical formation. After an incubation period of 35 min in 50 μM compound 1, the depression of the cellular Rhodamine 123 fluorescence reached its maximum and amounted to about one-third of the control values without compound 1 (Tab. 2). The effect of compound 1 at incubation times of over 15 min is significant ($p < 0.05$ in the t-test) in all measurements.

TABLE 2

Effect of 50 μM compound 1 on free radical formation by cultured microglia cells.

| Min | Control | Compound 1 | % Inhibition |
|---|---|---|---|
| 15 | 2190.4 | 2060.6 | — |
|  | (19.5) | (102.3) |  |
| 25 | 2626.7 | 2121.3 | 19* |
|  | (227.4) | (21.4) |  |
| 35 | 1602.2 | 1170.4 | 27* |
|  | (125.1) | (27.3) |  |
| 45 | 2029.5 | 1556.9 | 23* |
|  | (283.5) | (151.9) |  |
| 60 | 1239.2 | 910.4 | 27* |
|  | (108.1) | (24.4) |  |

The numerical values (mean values ± S.D. in brackets) give the fluorescence values as apparatus-specific units.
*Statistically significantly different from control $p < 0.05$ t-test.

EXAMPLE 2

Preparation of 1-(5-oxohexyl)-3-methyl-7-n-propylxanthine (Compound 1)

437.2 g of 3-methyl-7-propylxanthine, suspended in a mixture of 240 g of methanol and 321 g of water, are brought into solution at elevated temperature using 160 g of 50% strength sodium hydroxide solution, 358 g of 1-bromo-5-hexanone are subsequently added at boiling point and the mixture is heated under reflux for 4½ hours. After cooling, unreacted 3-methyl-7-propylxanthine is separated off and the alcohol is removed by distillation. The aqueous solution is adjusted to pH 11 with sodium hydroxide solution and extracted with methylene chloride. After recrystallizing from 5.2 l of diisopropyl ether, 1-(5-oxohexyl)-3-methyl-7-propylxanthine of melting point 69°-70° C. is obtained from the residue of the methylene chloride solution in about 90% yield (based on reacted 3-methyl-7-propylxanthine).

EXAMPLE 3

Preparation of 7-ethoxymethyl-1-(5-hydroxy-5-methylhexyl)xanthine a) 48.4 g (0.02 mol) of 3-benzylxanthine are dissolved hot in a solution of 8 g (0.2 mol) of sodium hydroxide in 200 ml of water. After filtration, the mixture is concentrated in vacuo, methanol is distilled over several times and the sodium salt is dried in a high vacuum.

The dry salt is suspended in 0.6 l of dimethylformamide (DMF), 18.92 g (0.2 mol) of ethoxymethyl chloride are added with stirring and the mixture is stirred at 110° C. for 18 hours. It is then filtered hot, the filtrate is evaporated in vacuo, the residue is dissolved in 500 ml of 2N sodium hydroxide solution and the solution is extracted by shaking with chloroform to remove 1,7-dialkylated 3-benzylxanthine formed as a by-product. The alkaline aqueous solution is brought to pH 9 with 2N hydrochloric acid with stirring, and the crystallizate formed is filtered off with suction, first washed with water until chloride-free and then with methanol and dried in vacuo.

Melting point: 136°-138° C.
$C_{15}H_{16}N_4O_3$ (MW = 300.3)

b) 15 g of the 7-ethoxymethyl-3-benzylxanthine obtained in a) are mixed with 7.5 g (0.054 mol) of potassium carbonate and 8.2 g (0.054 mol) of 1-chloro-5-hydroxy-5-methylhexane (prepared as in U.S. Pat. No.

4,833,146) in 300 ml of DMF and the mixture is heated to 110° C. with stirring for 5 hours. The mixture is filtered hot with suction and concentrated, and the residue is taken up in chloroform, the solution is washed first with 1N sodium hydroxide solution and then with water until neutral and dried over sodium sulfate. The solvent is removed by distillation under reduced pressure and the residue is recrystallized from diisopropyl ether with the addition of ethyl acetate.

Yield: 19.1 g (92.3% of theory)
Melting point: 96°–97° C.
$C_{22}H_{30}N_4O_4$ (MW=414.5)

c) 4.14 g (0.01 mol) of the 7-ethoxymethyl-1-(5-hydroxy-5-methylhexyl)-3-benzylxanthine obtained in b) are hydrogenated with shaking in 100 ml of ethanol, 75 ml of water and 5 ml of conc. $NH_4OH$ solution over 1.5 g of palladium (10%) on active carbon at 60° C. and 3.5 bar for 198 hours. After cooling, the mixture is blanketed with nitrogen, the catalyst is filtered off, the filtrate is concentrated and the solid residue is recrystallized from ethyl acetate.

Yield: 2.6 g (80.1% of theory)
$C_{15}H_{24}N_4O_4$ (MW=324.4)

EXAMPLE 4

Preparation of 1-(5-hydroxy-5-methyl)xanthine a) 36.3 g (0.15 mol) of 3-benzylxanthine, and 3.6 g (0.15 mol) of NaH are stirred at 45° C. in 500 ml of DMF. 25.6 g of benzyl bromide dissolved in 45 ml of DMF are then added dropwise and the mixture is heated at 100°–110° C. for 5 hours. The product is then further purified as in example 3a).

b) 19.9 g (0.06 mol) of the 3,7-dibenzylxanthine obtained in a), 8.3 g of potassium carbonate and 10 g (0.065 mol) of 1-chloro-5-hydroxy-5-methylhexane in 350 ml of DMF are heated at 110°–120° C. with stirring for 8 hours and further purified as described in 3b).

c) 4.46 g (0.01 mol) of the 3,7-dibenzyl-1-(5-hydroxy-5-methylhexyl)xanthine obtained in b) are reacted for 163 hours as described in example 3c) and correspondingly further purified.

Yield: 1.53 g (57.5% of theory)
Melting point: 238°–239° C.
$C_{12}H_{18}N_4O_3$ (MW=266.3)

We claim:
1. A pharmaceutical for the treatment of disorders which can occur after cranio-cerebral traumas, which comprises an effective content of at least one xanthine derivative of the formula I

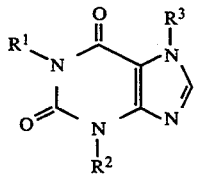

and/or at least one of its physiologically tolerable salts, in which $R^1$ is
 a) oxoalkyl having 3 to 8 carbon atoms, whose carbon chain can be straight-chain or branched,
 b) hydroxyalkyl having 1 to 8 carbon atoms, whose carbon chain can be straight-chain or branched and whose hydroxyl group is a primary, secondary or tertiary alcohol function, or
 c) alkyl having 1 to 6 carbon atoms, whose carbon chain can be straight-chain or branched, $R^2$ is
 a) hydrogen or
 b) alkyl having 1 to 4 carbon atoms, whose carbon chain can be straight-chain or branched, $R^3$ is
 a) hydrogen,
 b) alkyl having 1 to 6 carbon atoms, whose carbon chain is interrupted by an oxygen atom, or
 c) oxoalkyl having 3 to 8 carbon atoms, whose carbon chain can be straight-chain or branched.

2. A pharmaceutical as claimed in claim 1, which contains at least one xanthine derivative of the formula I, in which
$R^1$ is
 a) oxoalkyl having 4 to 6 carbon atoms, whose carbon chain is straight-chain or branched, or
 b) alkyl having 3 to 6 carbon atoms,
$R^3$ is
 a) alkyl having 1 to 4 carbon atoms or
 b) oxoalkyl having 3 to 6 carbon atoms, and/or at least one of the physiologically tolerable salts of the xanthine derivative of the formula I.

3. A process for the production of a pharmaceutical as claimed in claim 1 for the treatment of disorders which can occur after cranio-cerebral traumas, which comprises bringing at least one xanthine derivative of the formula I and/or at least one of its physiologically tolerable salts into a suitable administration form using a physiologically acceptable excipient and further suitable active substances, additives or auxiliaries.

4. A xanthine derivative of the formula I

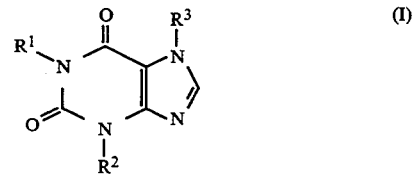

in which
$R^1$ is
 a) oxoalkyl having 3 to 8 carbon atoms, whose carbon chain can be straight-chain or branched, or
 b) hydroxyalkyl having 1 to 8 carbon atoms, whose carbon chain can be straight-chain or branched and whose hydroxyl group is a primary, secondary or tertiary alcohol function,
$R^2$ is hydrogen,
$R^3$ is
 a) hydrogen,
 b) alkyl having 1 to 6 carbon atoms, whose carbon chain can be straight-chain or branched,
 c) alkyl having 1 to 6 carbon atoms, whose carbon chain is interrupted by an oxygen atom, or
 d) oxoalkyl having 3 to 8 carbon atoms, whose carbon chain can be straight-chain or branched.

5. A xanthine derivative of the formula I as claimed in claim 4, in which
$R^1$ is hydroxyalkyl having 1 to 8 carbon atoms, whose carbon chain can be straight-chain or branched and whose hydroxyl group is a primary, secondary or tertiary alcohol function,
$R^2$ is hydrogen, R³ is
 a) hydrogen,
 b) alkyl having 1 to 6 carbon atoms, whose carbon chain is interrupted by an oxygen atom.

6. A method of treating secondary brain damage comprising:
administering an effective amount of a xanthine derivative of the formula I

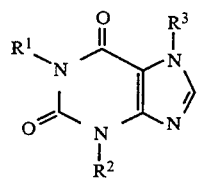

and/or at least one of its physiologically tolerable salts,
wherein R¹ is oxoalkyl having 3 to 8 carbon atoms, whose carbon chain can be straight-chain or branched; hydroxyalkyl having 1 to 8 carbon atoms, whose carbon chain can be straight-chain or branched and whose hydroxyl group is a primary, secondary or tertiary alcohol function; or alkyl having 1 to 6 carbon atoms, whose carbon chain can be straight-chain or branched;
R² is hydrogen; or alkyl having 1 to 4 carbon atoms, whose carbon chain can be straight-chain or branched;
R³ is hydrogen; alkyl having 1 to 6 carbon atoms, whose carbon chain can be straight-chain or branched; alkyl having 1 to 6 carbon atoms, whose carbon chain is interrupted by an oxygen atom; or oxoalkyl having 3 to 8 carbon atoms, whose carbon chain can be straight-chain or branched;
wherein said secondary brain damage results from biochemical events leading to brain cell death which occur after cranio-cerebral trauma.

7. The method of claim 6, wherein at least one xanthine derivative of the formula I is employed wherein
R¹ is oxoalkyl having 4 to 6 carbon atoms, whose carbon chain is straight-chain; or alkyl having 3 to 6 carbon atoms;
R² is alkyl having 1 to 4 carbon atoms;
R³ is alkyl having 1 to 4 carbon atoms; or oxoalkyl having 3 to 6 carbon atoms, and/or at least one of its physiologically tolerable salts.

8. The method of claim 6, wherein the xanthine derivative is 1-(5-oxohexyl)-3-methyl-7-n-propyl xanthine or at least one of its physiologically tolerable salts.

9. A method of treating secondary brain damage comprising:
administering an effective amount of a pharmaceutical composition containing a xanthine derivative of the formula I

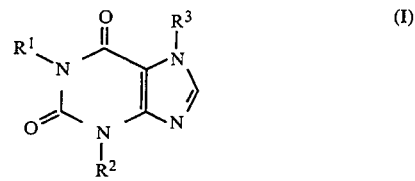

and/or at least one of its physiologically tolerable salts,
wherein R¹ is oxoalkyl having 3 to 8 carbon atoms, whose carbon chain can be straight-chain or branched; hydroxyalkyl having 1 to 8 carbon atoms, whose carbon chain can be straight-chain or branched and whose hydroxyl group is a primary, secondary or tertiary alcohol function; or alkyl having 1 to 6 carbon atoms, whose carbon chain can be straight-chain or branched;
R² is hydrogen; or alkyl having 1 to 4 carbon atoms, whose carbon chain can be straight-chain or branched;
R³ is hydrogen; alkyl having 1 to 6 carbon atoms, whose carbon chain can be straight-chain or branched; alkyl having 1 to 6 carbon atoms, whose carbon chain is interrupted by an oxygen atom; or oxoalkyl having 3 to 8 carbon atoms, whose carbon chain can be straight-chain or branched;
wherein secondary brain damage results from biochemical events leading to brain cell death which occur after cranio-cerebral trauma.

10. The method according to claim 9, wherein the pharmaceutical composition is in a suitable administration form using a physiologically acceptable excipient and further suitable active substances, additives or auxiliaries.

11. The method according to claim 6, wherein said secondary brain damage is caused by macrophages which release histotoxic substances.

12. The method according to claim 6, wherein said secondary brain damage is caused by the activation of microglia cells.

13. The method according to claim 9, wherein said secondary brain damage is caused by macrophages which release histotoxic substances.

14. The method according to claim 9, wherein said secondary brain damage is caused by the activation of microglia cells.

* * * * *

UNITED STATES PATENT AND TRADEMARK OFFICE
CERTIFICATE OF CORRECTION

PATENT NO. : 5,409,935
DATED : April 25, 1995
INVENTOR(S) : Hans-Peter SCHUBERT et al It is certified that error appears in the above-indentified patent and that said Letters Patent is hereby corrected as shown below:

Claim 1, Column 10, delete lines 5 & 6 entirely.

Signed and Sealed this

Twenty-first Day of November, 1995

Attest:

BRUCE LEHMAN

Attesting Officer

Commissioner of Patents and Trademarks